(12) United States Patent
Andersson et al.

(10) Patent No.: US 11,055,884 B2
(45) Date of Patent: Jul. 6, 2021

(54) METHOD, COMPUTER PROGRAM PRODUCT AND COMPUTER SYSTEM FOR CORRECTING A CT IMAGE

(71) Applicant: RaySearch Laboratories AB, Stockholm (SE)

(72) Inventors: Sebastian Andersson, Stockholm (SE); Rasmus Nilsson, Stockholm (SE); Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 16/757,224

(22) PCT Filed: Oct. 16, 2018

(86) PCT No.: PCT/EP2018/078150
§ 371 (c)(1),
(2) Date: Apr. 17, 2020

(87) PCT Pub. No.: WO2019/076846
PCT Pub. Date: Apr. 25, 2019

(65) Prior Publication Data
US 2020/0279414 A1    Sep. 3, 2020

(30) Foreign Application Priority Data

Oct. 22, 2017  (EP) .................................... 17197663

(51) Int. Cl.
*G06T 11/00* (2006.01)
*G16H 20/40* (2018.01)
(Continued)

(52) U.S. Cl.
CPC ............ *G06T 11/008* (2013.01); *A61B 6/032* (2013.01); *A61B 6/4085* (2013.01); *A61N 5/1039* (2013.01); *G06F 16/53* (2019.01); *G06T 7/0014* (2013.01); *G16H 20/40* (2018.01); *G16H 30/40* (2018.01); *G16H 50/70* (2018.01);
(Continued)

(58) Field of Classification Search
CPC .................................................... G06T 11/008
See application file for complete search history.

(56) References Cited

U.S. PATENT DOCUMENTS

2007/0086678 A1   4/2007   Chefd'hotel et al.
2012/0263360 A1   10/2012  Zhu et al.
(Continued)

OTHER PUBLICATIONS

Nithiananthan, Sajendra et al., "Demons deformable registration of CT and cone-beam CT using an iterative intensity matching approach," Med. Phys. 38 (4), 2011 (first published Mar. 8, 2011), pp. 1785-1798.
(Continued)

*Primary Examiner* — Oneal R Mistry
(74) *Attorney, Agent, or Firm* — Faegre Drinker Biddle & Reath LLP (57) ABSTRACT

A method of correcting a first CT image for shading artefacts using another CT image as reference, comprising the steps of creating a difference image between the images and a correction map based on the difference image. The correction map is used to correct the first CT image. A method of converting a CT image to the value range of another CT image is also disclosed.

14 Claims, 8 Drawing Sheets

(51) Int. Cl.
*G16H 50/70* (2018.01)
*G16H 30/40* (2018.01)
*G06F 16/53* (2019.01)
*A61B 6/03* (2006.01)
*A61B 6/00* (2006.01)
*A61N 5/10* (2006.01)
*G06T 7/00* (2017.01)

(52) U.S. Cl.
CPC ............... *G06T 2207/20224* (2013.01); *G06T 2207/30008* (2013.01); *G06T 2210/41* (2013.01); *G06T 2211/424* (2013.01)

(56) References Cited

U.S. PATENT DOCUMENTS

2014/0029831 A1  1/2014  Blaskovics et al.
2016/0022240 A1* 1/2016  Yamagata ............ A61B 6/486
                                                    382/131
2017/0049379 A1* 2/2017  Luo ..................... G06K 9/4604
2017/0365058 A1* 12/2017 Kabus ................... G06T 7/344

OTHER PUBLICATIONS

T E Marchant, et al., "Shading correction algorithm for improvement of cone beam CT images in radiotheraphy." Physics in Medicine and Biology 53, 2008, pp. 5719-5733.

European Search Report dated Jun. 1, 2018 (completed May 15, 2018) in the corresponding EP 17 19 7663.

Wu, Pengwei et al., "Iterative CT shading correction with no prior information," Phys. Med. Biol., 60 (2015) 8437-8455.

Shi, Linxi et al., "Fast shading correction for cone beam CT in radiation therapy via sparse sampling on planning CT," Med. Phys. 44 (5), May 2017, pp. 1796-1808.

* cited by examiner

METHOD, COMPUTER PROGRAM PRODUCT AND COMPUTER SYSTEM FOR CORRECTING A CT IMAGE

This application is the National Stage of International Application No. PCT/EP2018/078150, filed Oct. 16, 2018, and claims benefit of European Patent Application No. 17197663.2, filed Oct. 22, 2017, the entire contents of which are incorporated by reference herein.

TECHNICAL FIELD

The present invention relates to methods for improving adaptive radiotherapy as well as computer program products and a computer system in which such methods may be implemented.

BACKGROUND

In radiotherapy treatment, the treatment is given in a number of sessions, called fractions. Before the treatment starts, the treatment plan to be used is generated, based on high-resolution images which are typically CT images. Before each fraction, a new image, typically a cone beam CT (CBCT) image, is often taken to ensure correct positioning of the patient. These images can also be used in adaptive radiotherapy, wherein the images are used to calculate the actually delivered dose (given the up to date patient information). To be able to relate the dose in the new images to the planned dose, the CBCT images are registered (preferably deformably) with the planning CT. CBCT images typically have pronounced artefacts, which introduce errors in the calculated dose. These artefacts thus have to be corrected for if an accurate dose is to be found based on these images.

The term CT image in this document can be taken to mean any type of CT image, including conventional CT images, helical CT images, and CBCT images.

Knowing the attenuation coefficients of different types of tissue traversed by radiation is important for dose computation in treatment planning. For conventional CT images, the relationship between densities or electron densities and Hounsfield units (HU) is found for the CT protocol used. This relationship is quite stable and does not usually vary between patients. Density or electron density values are needed for dose computation. It is difficult to establish a similar relationship between a CBCT image and the electron density HU scale, since a CBCT density table will be dependent on the size of the imaged object. This, in addition to the artefacts mentioned above, makes dose computation based on CBCT images more difficult.

The planning CT image and subsequent CBCT images will differ, when comparing them through a registration, for three main reasons: anatomical differences, registration errors and image artefacts. Image artefacts are primarily present in the CBCT. In particular, shading artefacts result in that the same tissue type is given varying values depending on its spatial location in the image. When processing the CBCT image, the differences caused by shading artefacts should be handled, since they produce relatively large dose computation errors. Differences caused by actual anatomical differences (e.g. mismatching air cavities or misaligned bone) or deformation errors should be ignored when using the planning CT to correct the CBCT. Therefore, it is important to differentiate between the three kinds of differences.

T E Marchant et al., Shading correction algorithm for improvement of cone-beam CT images in radiotherapy, Phys. Med. Biol. 53 (2008) 5719-5733, discloses a method of converting the values of a CBCT image to HU values based on a CT image of the same anatomical region. This article proposes to obtain a difference image and to filter out the high-frequency changes using a boxcar averaging algorithm on this difference image before applying it to the CBCT image. This method is quite sensitive to the performance of the conversion step. Also, the correction sometimes includes other differences than the artefacts. Further, the method necessitates the use of two masks, one for bone and one for other tissue.

Pengwei Wu et al., Iterative CT shading correction with no prior information, Phys. Med. Biol., 60 (2015) 8437-8455 proposes a method of eliminating artefacts in any type of CT image, including CBCT, using a template generated from the image based on general knowledge about typical value range in a CT image. The CT image is segmented and corrected, using the template as a reference. This method requires a segmentation algorithm and the quality of the segmentation directly influences the output quality. Further, the method is dependent on a good approximation of what tissues the patient consists of Shi et al., Fast shading correction for cone beam CT in radiation therapy via sparse sampling or planning CT, Med. Phys. 44 (5), May 2017, 0094-2405/2017/44(5)/1796/13, proposes a method for correcting shading artefacts in a CBCT image using information from a planning CT image. The method is based on a coarse mapping between the CBCT and CT images to obtain a difference image, and selection of sparse shading samples for correction using empirical constraints. Local filtration is used to process the sparse data to obtain a shading map which is used to correct the CBCT to obtain a CBCT image corrected for shading artefacts. This method depends on the assumption that the images are on the same scale, which may not always be the case. Also, the method is sensitive to noise and large artefacts.

SUMMARY

It is an object of the present invention to enable the correction of a CT image, such as a CBCT image, for artefacts, in particular shading artefacts.

According to a first aspect, the invention relates to a method of correcting a first CT image for artefacts, using a second CT image as a template, while maintaining the anatomical information in the first CT image. The CT images may be any types of CT images. Typically, the image used as a template will be of a higher quality than the image being corrected. In a preferred application, the first CT image may be a CBCT image and the second CT image may be a conventional, or helical CT image. The method is based on the insight that the shading artefacts typically vary with a low spatial frequency while the differences caused by displacement or geometrical changes normally vary with a higher spatial frequency.

If the images are not of the same modality, or do not use the same value range, it may be necessary to convert one of the images before the correction. For this conversion, the conversion method according to the second aspect is particularly suitable. In the typical situation where a CBCT image is corrected using a CT image as reference, it may be useful to convert the CBCT image to the value range of the CT image. According to a second aspect, a suitable conversion method is proposed. This method may also be used for other purposes.

According to the first aspect, the invention relates to a method of correcting a first CT image for artefacts, comprising the steps of
 a) Providing the first CT image and a corresponding second CT image as an original first and second CT image, respectively and letting the original first CT image be the current first CT image,
 b) Providing data representing a registration between the images,
 c) Ensuring that the first and the second CT image form a value matched image pair, which use the same value range, if necessary by converting one of them to match the other,
 d) Obtaining a difference image D between the images of the value matched image pair,
 e) Defining an image mask M defining which voxels to consider in the difference image,
 f) Obtaining a final correction map Cf by iteratively performing a loop comprising in each iteration at least one of the following steps:
   i. Defining the correction map C based on the difference image and optionally the image mask M,
   ii. Updating the final correction map Cf,
   iii. Updating the current first CT image using the correction map and using the updated image as the current first CT image,
   iv. Updating the image mask M based on information from the correction map, the difference image and/or the current first and second CT image,
   v. Updating the first or second CT image of the value matched image pair based on the current first CT image,
   vi. Calculating a difference image between the updated second CT image and the current first CT image,
 g) Applying the final correction map to the original first CT image or to the current first CT image, to obtain a corrected first CT image.

According to the first aspect, the influence from artefacts, which occur in lower quality images such as CBCT images will be reduced. At the same time, other differences between the images, caused by anatomical changes or registration errors, which often give small shifts between corresponding structures in the two images, will be identified so that the correction will not compensate for such differences but only the differences that are actually due to artefacts. This, for example, makes it possible to obtain a CBCT image that is suitable for dose computation in radiotherapy planning by using a planning CT image taken earlier as reference. Typically, a planning CT image will be a conventional or helical CT image.

The original first and second CT images are typically unmodified images and the first image is assumed to need corrections because of artefacts. Normally the procedure includes storing these images for use later in the procedure. If the images do not use the same value range, the step of ensuring that the images use the same value range comprises converting one of the images to the value range used in the other image. For example, the second CT image may be converted to the value range of the first CT image, so that the value matched image pair comprises the values of the first CT image and of a transformed second CT image tCT. Alternatively, the first CT image may be converted to the value range of the second CT image, so that the value matched image pair comprises values of the second CT image and of the transformed first CT image tCBCT.

In step iii, the current first CT image may be formed iteratively by applying correction maps to an image that is updated stepwise by each correction map. Alternatively, the current first CT image may be formed by applying a sum of several correction maps, or the current information stored in the final correction map, to the original first CT image.

The conversion, if necessary, is typically performed by means of a transformation representation such as a function, a lookup table (LUT) or a diagram, said transform representation mapping a value in the first CT image to a value in the second CT image or vice versa, and applying that transformation representation to the image that is to be converted. A particularly suitable conversion method is described below, according to the second aspect of the invention. In step v of the method above, a new conversion between the first CT image and second CT image may be performed after the updating of the first CT image. This may be advantageous since the first CT image has then been improved, which will result in a better transformation result.

In a preferred embodiment the second CT image, which is used as a reference, is based on Hounsfield units, since this is the value scale used in most CT images. Preferably a deformable registration method is used, since this will produce a more correct result. However, a rigid registration may also be used.

In a preferred embodiment, the image mask is defined so that it includes voxels for which the corresponding voxels in the difference image contain information about the artefacts to be corrected for, whilst excluding voxels containing information irrelevant to the correction. For example, the image mask may include voxels for which the difference is below a threshold value and excludes voxels for which the difference is above the threshold value It is often suitable to perform some of the steps of the loop i.-vi. a number of times to produce the image mask M and then perform another selection of the steps a number of times then to produce the final correction map C. For example, a suitable sequence of steps for producing the image mask has been found to be
 Steps i, iv, possibly iterated one or more of times
 Steps i, iii, iv, v, vi possibly iterated one or more of times
 Steps i and iv, possibly iterated one or more times
 Steps i, iii, iv, v, vi.
A suitable sequence of steps for finding the correction map C has been found to be:
 Optionally resetting the first CT image to the original first CBCT image and preferably updating the difference image, that is, perform step vi.
 Steps i, ii, iii, v, vi possibly iterated one or more times
The second aspect of the invention relates to a method of creating a transformation representation which may be used for converting a first CT image by a method including registration with a corresponding, second CT image, for example, a planning CT image, which is normally of higher quality and based on values enabling dose computations, that is, values reflecting the densities or electron densities.

A method according to this second aspect is a method of creating a representation of a transformation between a first CT image of an object and a second CT image of the object, said first CT image using a first CT value range and said second CT image using a second CT value range different from the first CT value range, said method comprising
 a) Providing the first and the second CT image and providing data representing a registration between the first and the second CT image.

b) Creating a joint histogram based on the registration data provided in step a)

c) Based on the joint histogram obtained in step b), identifying at least two tissue value pairs, each corresponding to a type of tissue found in the imaged object d) Based on at least some of the value pairs identified in step c), creating the representation of a transformation from the first CT image to the second CT image and/or vice versa.

Either the first or the second CT image may be a CBCT image and the other CT image may be a conventional or helical CT.

Preferably the method comprises the steps of creating a CT histogram of the occurrences of values in one of the images and, based on the occurrences, selecting the number of tissue value pairs to be found in step c) and optionally restricting the area in the joint histogram for step c).

The voxels to be used in step c) are preferably selected as voxels having a value below a set threshold, preferably corresponding to the density of bone tissue. For determining one or more tissue value pairs for bone, preferably a line is identified for values above the threshold, for example using the RANSAC method. A particularly good result is achieved if the step of identifying the line comprises forcing the line to pass through the point corresponding to the tissue value pair with the highest density below the bone density threshold. It should be noted that the term tissue value pairs may refer to any value pair designating the same material, not only tissue, for example air, water or phantom material.

The data representing the registration is preferably based on a deformable registration of the images but it may also be based on a rigid registration.

According to the second aspect of the invention, using the transformation representation, the first CT image may be converted, fully automatically, to an image on which dose computations may be performed, while keeping the geometry as in the first CT image. Fully automatic in this context means that no manual interaction or segmentation of the images used will be necessary.

The method is particularly suitable for converting CBCT images, which are often used to provide updated information during adaptive treatment, to a value range that may be used for dose computation. The converted CBCT image can be more easily compared to the CT image. Of course, a conversion from CT to CBCT can also, or alternatively, be obtained, or between any two images of the same object, or region of a patient.

The iterative nature of the inventive methods leads to more correct results, and in particular, the iterations will mitigate the negative effects of imperfect correction algorithms. By gradually creating the correction map it is easier to dismiss the voxels, in which the difference is due to anatomical changes, from contributing to the correction map. An iterative approach, where the both the conversion and correction are included in each iteration, gives the possibility to correct potential faults in the conversion and correction step in later iterations.

The invention also relates to a computer program product comprising computer readable code means which when run in a processor will cause the processor to perform any one of the methods disclosed above. As is common in the art the computer program product may be stored on any suitable storage means such as a non-transitory storage means.

The invention also relates to a computer system comprising a processing means, at least one program memory holding at least one computer program as outlined above and at least one data memory holding data to be used in the method.

BRIEF DESCRIPTION OF THE DRAWINGS

The invention will be described in more detail in the following, by way of example and with reference to the appended drawings, in which.

DETAILED DESCRIPTION

Figure 1A:
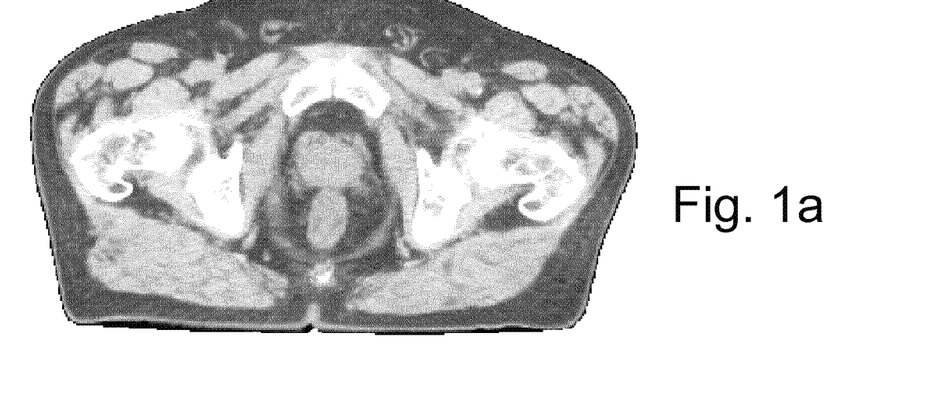
FIGS. 1a-1g are examples of different types of images used in embodiments of the present invention

FIG. 1a shows a CT image that may be used in aspects of the present invention. Typically, the CT image is obtained before treatment and used in treatment planning. As is common in the art, the CT image shows the attenuation coefficient of the tissue in each voxel as Hounsfield Units (HU). The attenuation coefficient is related to density. Throughout this description, density or electron density, or any suitable scale that is related to one of them, may be used instead of Hounsfield Units.

The following description is based on converting between CBCT and CT, for simplification and clarity. It should be understood that the image referred to as CBCT in the description may also be a CT image of any other type of CT modality. Typically, however, the image to be converted and/or corrected has a lower quality, for example more shading artefacts, than the image used as reference in the correction and/or conversion.

Figure 1B:
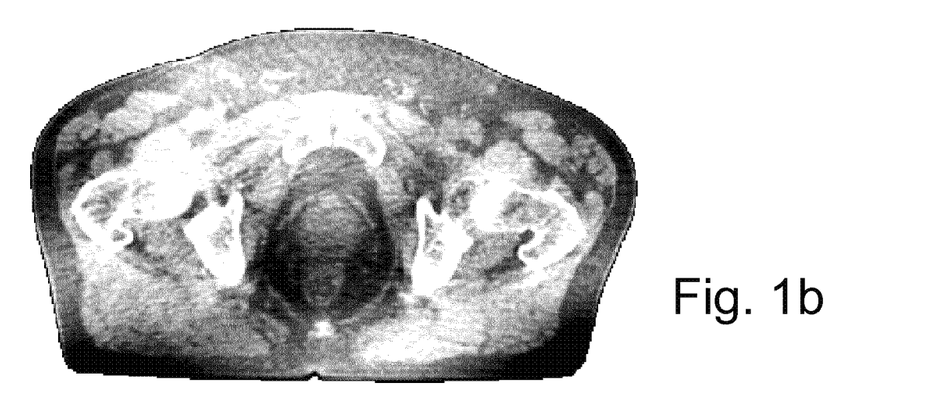

FIG. 1b shows a CBCT image of the same region of the same patient, that has been converted to the same scale as the CT image. FIGS. 1a and 1b have normally been taken at different times so that there will probably be anatomical differences between them. Typically, a CBCT image is taken before each of the treatment fractions. Normally, the CBCT image uses a different scale for voxel values that does not match the HU scale, so that conversion is needed to enable comparison of the CT image and the CBCT image. Alternatively, the CBCT image may have been obtained on a scale similar to the HU scale, in which case conversion will not be necessary. As can be seen, FIGS. 1a and 1b show substantially the same geometry, but the CBCT image includes shading artefacts which will lead to inaccuracy in the dose computation. There are also minor differences caused by anatomical changes and/or slightly different positioning of the patient.

Figure 1C:
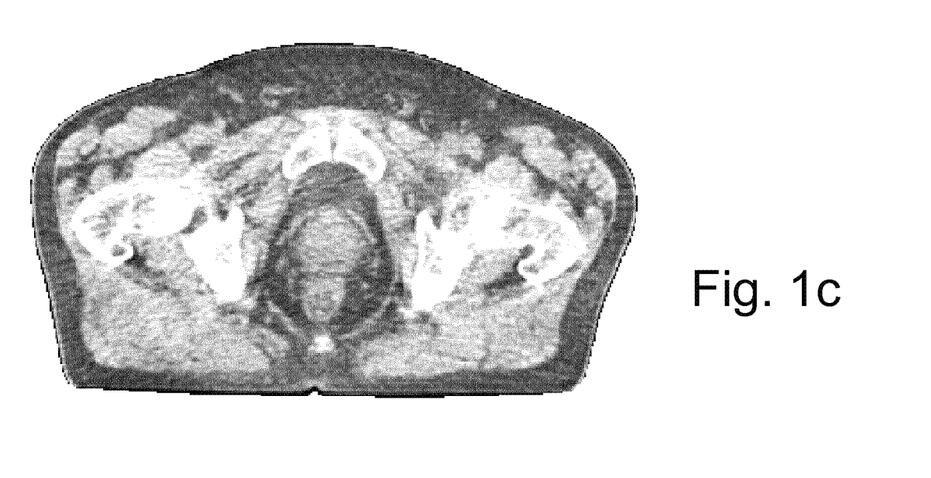
Figure 2:
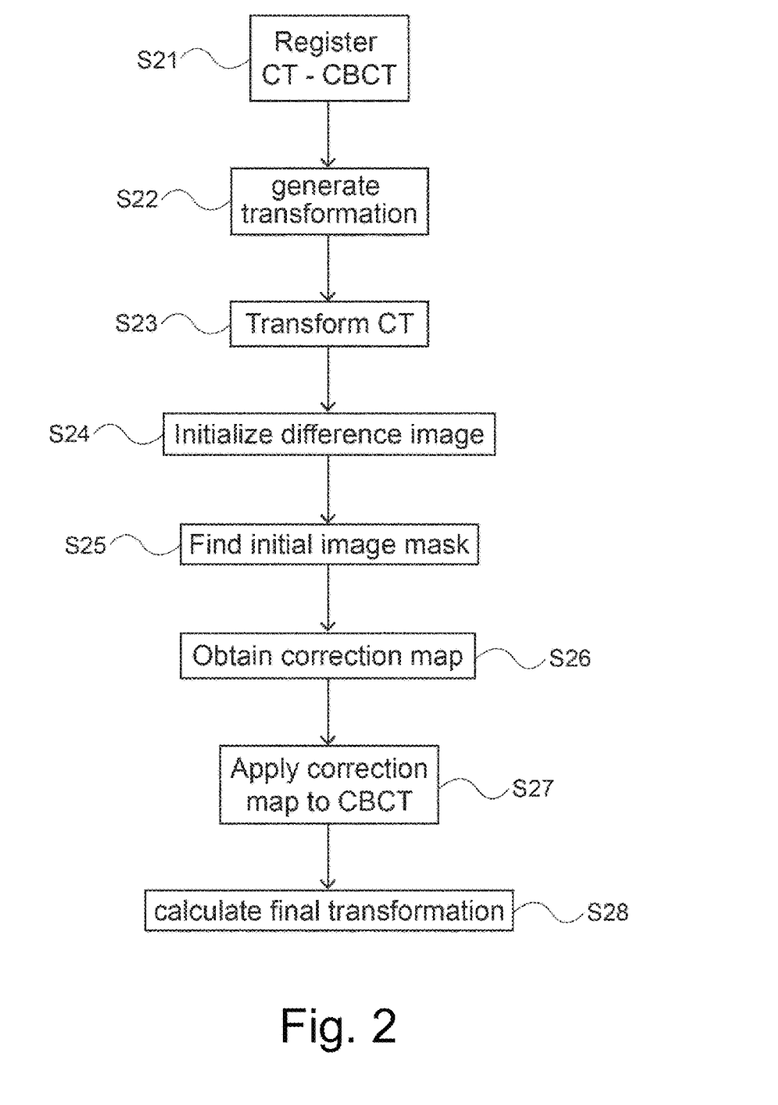
FIG. 2 is an overall flow chart of a method of obtaining a corrected CBCT image for use in dose computation

FIG. 1c is a new version of the CBCT image of FIG. 1b, corrected according to the process of FIG. 2 to be suitable for dose computations. The corrected CBCT image has the same geometry as the CBCT image of FIG. 1b, but is more similar to the CT image of FIG. 1a when it comes to voxel values, since artefacts have been reduced.

Figure 1D:
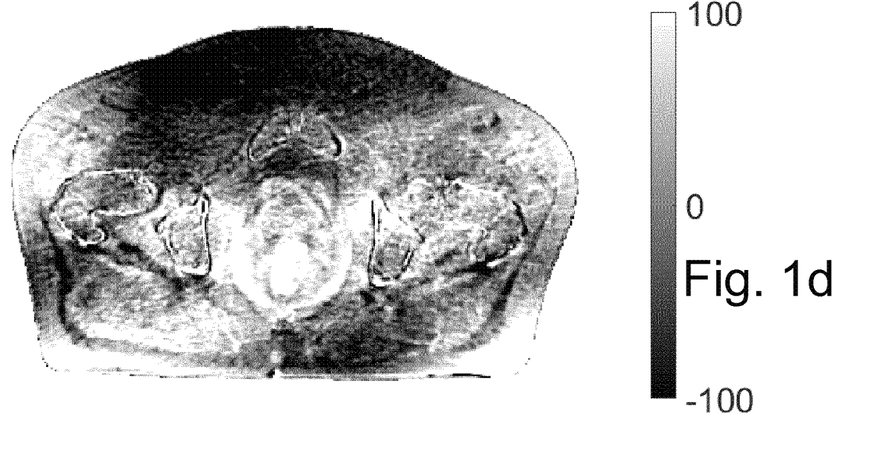

FIG. 1d shows a difference image after deformable registration, reflecting the value difference between each voxel in the CBCT image shown in FIG. 1b and the corresponding voxel in the CT image. In the difference image, as indicated by the scale to the right of the image, voxels that are similar in value between the images are shown in a grey colour. Differences are shown as increasingly bright colours for values that are lower in the CBCT image than in the CT image and increasingly dark colour, for values that are higher in the CBCT image than in the CT image. A higher colour difference from the centre grey colour marked with 0 indicates a greater difference in values. As can be seen, a significant portion of the image is either near white or near black, which indicates a large difference between the CT image and the CBCT image. Before using the information in the difference image to correct the CBCT image, it must be determined which differences are caused by artefacts in the CBCT image and which differences are caused by actual geometric changes. Only the differences caused by artefacts should be taken into account when correcting the CBCT image, and the voxels displaying such differences are included in an image mask.

Figure 1E:
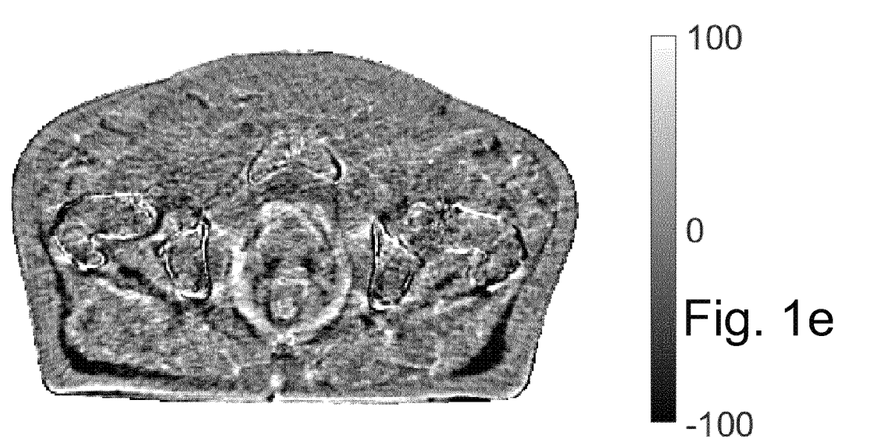

FIG. 1e shows a new difference image, created in the same way as FIG. 1d, but showing the difference between the CT image and the corrected CBCT image shown in FIG. 1c. As can be seen, the new difference image is grey over the majority of the image, indicating that the differences between corresponding voxels in the CT image and the corrected CBCT image are generally small.

Figure 1F:
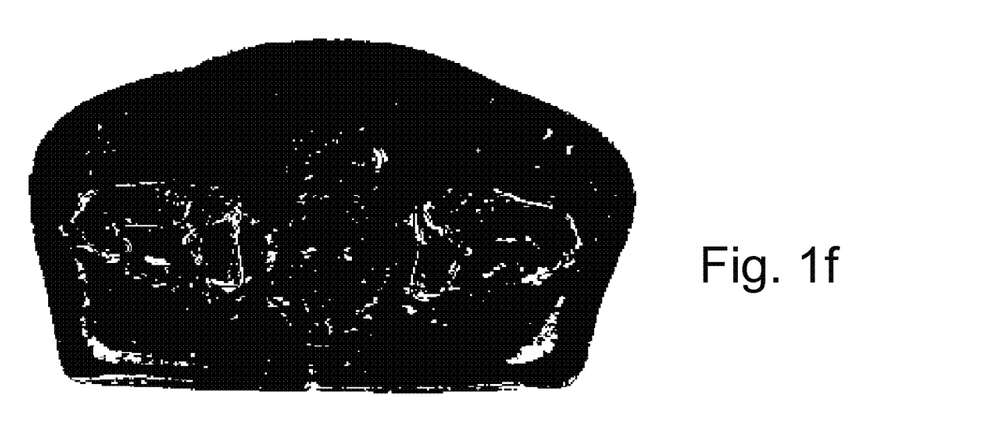

FIG. 1f is a mask used to select which voxels are to be taken into account in the correction. The white areas in the mask belong to voxels where the difference in voxel values are mainly due to anatomical differences and are thus not taken into account in the correction. The image mask is based on the difference image and may also include information from the tCT and CBCT and possibly from a correction map obtained earlier. How to obtain and use the mask will be discussed below.

Figure 1G:
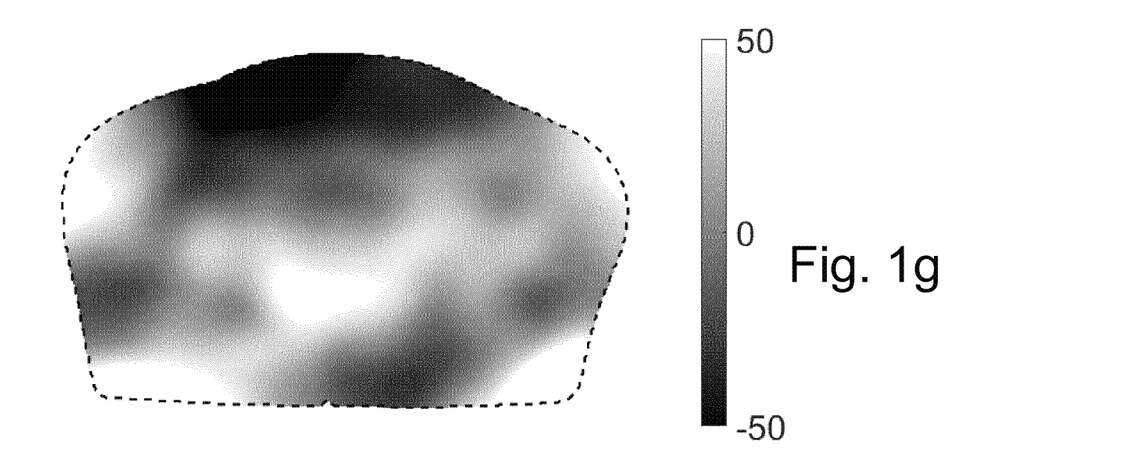

FIG. 1g is a correction map based on the mask of FIG. 1f, which may be obtained as discussed in connection with FIG. 3. The correction map indicates, by means of a grey scale, which areas of the CBCT image should be corrected and by how much. As indicated by the scale next to the image, a black or white region indicates that a large correction in the negative or positive direction, respectively, is necessary. The closer a region is to the colour matching the value 0 on the scale, the smaller correction is needed in that region.

In short, the process of creating a correction map based on the difference image is based on a filtering method involving identifying the areas in the difference image for which the difference between the CT value and the CBCT value is also caused by artefacts. This method effectively blurs a masked difference image only containing differences due to artefacts to effectively eliminate the remaining high spatial frequency changes, for example noise and anatomical changes not excluded by the mask. The changes that are due to low frequency artefacts are preserved and will be included in the correction map. For each iteration, the CBCT image is corrected using a correction map which is computed in each iteration. For each iteration, more and more of the low frequency artefacts will be removed and the values of the difference image will be closer and closer to zero. The resulting correction map is applied to the original CBCT image (FIG. 1b) to obtain the resulting CBCT image (FIG. 1d).

FIG. 2 is a flow chart of a method of obtaining a corrected CBCT image that is suitable for use in dose planning. As mentioned above, the method is also suitable for correcting other types of CT images, typically CT images of a lower quality than the ones used as reference in the correction.

In step S21 a CT image and a CBCT image of the same region of a patient are provided and registered, preferably deformably. The registration facilitates voxel-wise comparison and the creation of difference images. Typically, the CT image was obtained before the start of the treatment and used for treatment planning whereas the CBCT images are normally obtained before each treatment fraction. As explained above, the CT image normally has a known HU to density relationship whereas this is often not the case for CBCT images. The values typically vary in the same direction, that is, the same tissue types will have higher values, or lower values, respectively, in the two images.

Of course, the registration may have been performed in advance, in which case the registration data can be obtained and no registration has to be performed in this step. If a rigid registration was performed, the registration data will normally define a displacement and a rotation between the images. If a deformable registration was performed, the registration data will comprise a vector field defining the displacement of each voxel.

In step S22 a value transformation, facilitating a conversion between the CT and CBCT images, is obtained. If the image value ranges are sufficiently similar, this step may be skipped. The value transformation may for example be in the form of a lookup table matching values in the CT and CBCT images to each other. This may be done in any suitable manner. A particularly suitable way of creating the transformation is described in FIG. 4. In step S23 the CT image is transformed to an image denoted, tCT, by converting the values of the CT image to the corresponding CBCT values, using the transformation obtained in step S22. In step S24 a difference image D is initialized, where the difference between the values in each pairs of corresponding voxels is obtained. Hence D=tCT−CBCT.

The two images must use corresponding value ranges, but which one to choose may be selected depending on the desired result. Hence, instead of transforming the CT image in step S23, the CBCT image could be transformed to a transformed CBCT image tCBCT using the corresponding CT values. In that case the difference image generated in step S24 would be D=CT−tCBCT. Corresponding adaptations must be made in the rest of the flow chart of FIG. 2 and of FIG. 3, as will be obvious to the skilled person.

In step S25 an initial image mask M=M(D) is defined, to select which voxels are to be included in the correction. The image mask is based on the difference image and may also include information from the tCT and CBCT. M should include voxels containing differences that are due to CBCT shading artefacts but exclude voxels with differences caused by anatomical differences or deformation errors. In one embodiment, this is achieved by applying a threshold to D, so that voxels having a difference value smaller than the threshold are included in the mask and voxels having a greater difference value are disregarded. In another embodiment, segmentations of the two images may be used to identify voxels which belongs to the same segmented class. Voxels that belong to the same segmented class may be included, while voxels not belonging to the same class are disregarded.

In step S26 an iterative procedure is performed to obtain a final correction map Cf. An embodiment of this procedure is discussed in connection with FIG. 3.

In step S27 the final correction map obtained in step S26 is applied to the original CBCT to create a corrected CBCT, corrCBCT, where $$corrCBCT=CBCT+Cf$$

If, in step S23, the CT image was converted, the correction map can be applied directly to the CBCT image to produce the corrected CBCT image, as described above. If, in step S23, the CBCT image was converted, the correction map can be applied directly to the converted CBCT image to produce a converted, corrected CBCT image where the voxel values are according to the HU scale or have a defined relationship to the HU scale. Alternatively, in the latter case, the correction map may be converted to CBCT values and applied to the original CBCT image.

In step S28 a final value transformation is calculated based on the corrected CBCT image. This final value transformation is applied to the corrected CBCT image.

Figure 3:
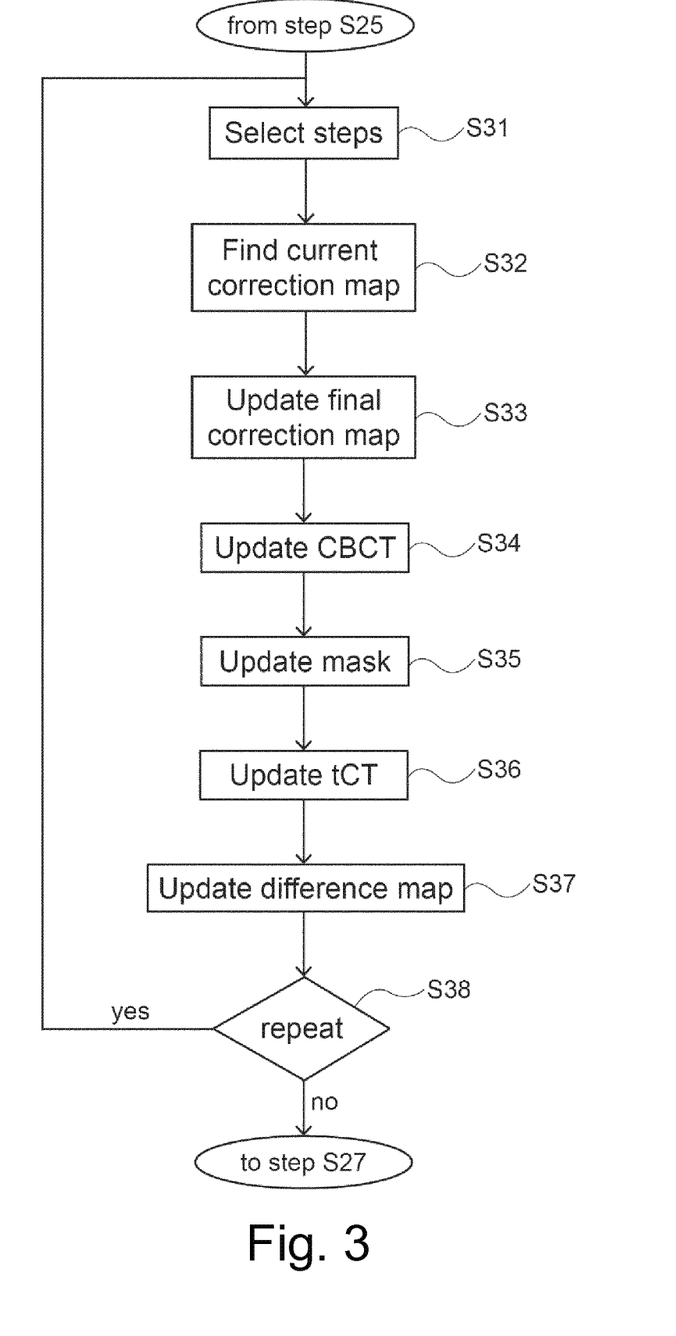
FIG. 3 is a flow chart detailing one of the steps in the flow chart of FIG. 2

FIG. 3 is a more detailed disclosure of an embodiment of the iterative procedure of step S26. Not all of the steps need to be performed in each iteration, as will be discussed below. Therefore, in a first step S31, input is taken from step S25, and it is determined which steps are to be run in the next iterations. The criteria for selecting steps will be discussed below.

In step S32 a correction map C is found by smoothing the masked difference image, that is, the difference image where voxels not included in the mask are disregarded. This is performed by any suitable method for smoothing the values and preferably also inserting suitable values where the mask does not include information on differences. This removes noise and sharp edges found in the difference image D and also fills in the areas not included in the mask M. This mask is originally obtained in step S25 but may be repeatedly updated in step S35 so in subsequent iterations of the procedure of FIG. 3 the latest updated mask is used.

In step S33, the correction map is used to update the final correction map, that is, Cf=Cf+C. The final correction map is the one that will be used in step S27. As will be understood this value is obtained through a number of iterations of FIG. 3.

In step S34, the CBCT image is updated using the correction map C, that is, the current CBCT is set to be CBCT+C.

In step S35, the mask M is updated to a mask based on the difference image and the correction map, that is M=M(D, C), or M=M(tCT, CBCT, C). In a preferred embodiment, the voxels in which the current correction will bring the difference below a certain threshold T are included by the mask, that is, voxels for which ABS(D−C)<T. It would also be possible to apply more complex decision criteria, for example based on the tCT and/or CBCT images.

In step S36, the value transformation is updated based on the current CBCT image, and the tCT is updated based on the updated value transformation. Of course, this only has to be done if the CBCT image has changed. In step S37 a new difference image is calculated D=tCT−CBCT, based on the current CBCT image.

Step S38 is a decision step to determine if the process of FIG. 3 should be repeated. If no, the procedure proceeds to step S27. If yes, the procedure returns to step S31, taking input values from the most recent iteration of the flow of FIG. 3. For example, the loop may terminate after a maximum number of iterations. Alternatively, convergence between the CT image and the CBCT image may be used as a criterion.

The decision in step S31 of which steps to run in the current iteration may be made based on different types of criteria.

It is feasible to run the loop first a number of times to define the mask and then to run the loop again a number of times to develop the correction map. The decision of what steps to include in a particular iteration depends on what should be the outcome of that particular iteration. If the loop is being run to create the mask, the number of voxels in the mask that were changed in the previous iteration may be used as a criterion. When the number of voxels that were changed is below a threshold value the iterations that are performed to create the mask may be stopped. If the loop is being run to determine the correction map, the convergence of Cf may be used as a criterion to stop the iterations.

Also, it should be determined which steps are to be run in the current iteration, depending on one or more of the current results, number of previous iterations, and/or if any of the variables should be reset to their original value. The value of constants, for example the threshold value, may also be changed depending on the current state. At one or more points during the iterations of the procedure of FIG. 3 it may be feasible to reset the CBCT values to keep the current mask, which has been improved for each iteration, while discarding the updated CBCT image, which has been updated based on an imperfect correction map.

A predetermined order of iterations could be set up, specifying which steps are to be performed in each iteration. One possible such setup, for first defining the mask and then the correction map, would be i. Run steps S32, S35, S38 a number of times, for example, four
ii. Run steps S32, S34, S35, S36, S37, S38
iii. Run steps S32, S35, S38 a number of times, for example, four
iv. Run steps S32, S34, S35, S36, S37, S38
v. Reset CBCT values and run S37
vi. Run steps S32, S33, S34, S36, S37, S38 a number of times, for example, four In the example above, a series of sequences i.-iv. are run to determine the mask M. When the mask has been determined, the CBCT values are reset to the original CBCT values in step v, and the last iterations, step vi, are run to determine the final correction map Cf that is to be applied to the CBCT image. As will be understood, the sequences, and the numbers of iterations, are merely examples and may be set in any way that is seen fit. For example, the number of iterations of each sequence will preferably be determined by convergence criteria, that is, how well the resulting mask, or the correction map, matches the desired result.

The converted CBCT image, as shown in FIG. 1b, may be obtained in any suitable way. In some cases, the CBCT image will already have values that are similar to the HU values used in the CT, in which case no conversion will be needed. In particular, as noted above, the image that is here referred to as CBCT may instead be an image of another CT modality, which uses values similar to that of the CT image used for correction.

A method of converting a CBCT image is disclosed in the following, with reference to FIG. 4. This method is suitable for use in the context of the method of FIG. 2 but can also be used in any context, for other purposes where a converted CBCT image is needed. A common way of converting the CBCT image is to create a value transformation, for example in the form of a lookup table (LUT) mapping values in the CBCT image to values in corresponding voxels of the CT image. Such a value transformation may be obtained in different ways.

Figure 4:
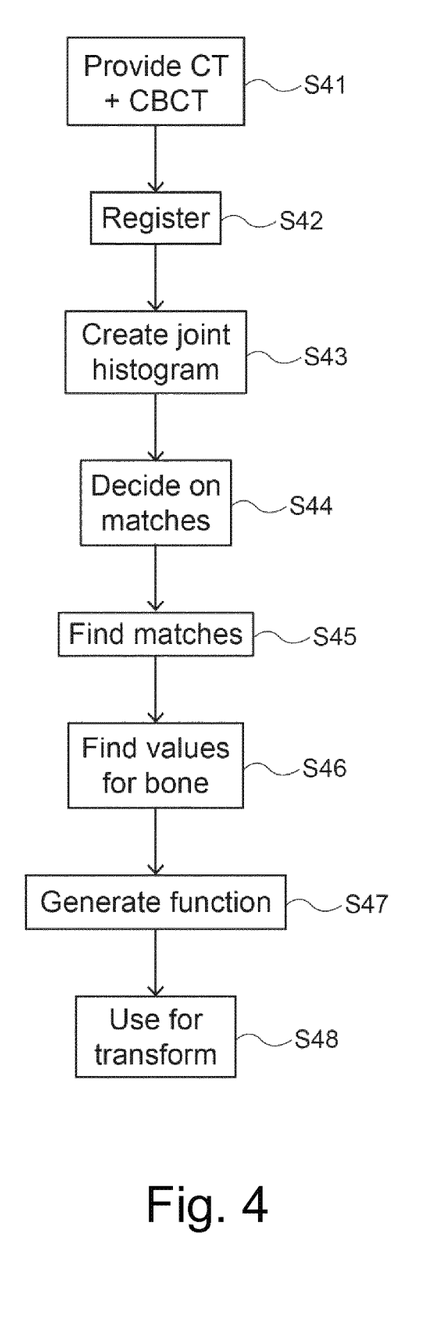
FIG. 4 is a flow chart of a method of converting a CBCT image to the value range of a conventional CT image

FIG. 4 discloses a method of obtaining a representation that may be used to perform a transformation from CBCT values to CT values, or vice versa. The representation may be presented in the form of a function, a lookup table, a diagram or in any other suitable way.

In step S41, the CT image and the CBCT image are provided. Typically, but not necessarily, the CT image has been obtained at an earlier stage, while the CBCT image is a more recent image. In step S42 the CT image and the CBCT image are registered, preferably using a deformable registration method. This will allow a point-wise mapping of the two images. As in Step S21, the registration may have been performed earlier, in which case registration data are provided instead.

Figure 5A:
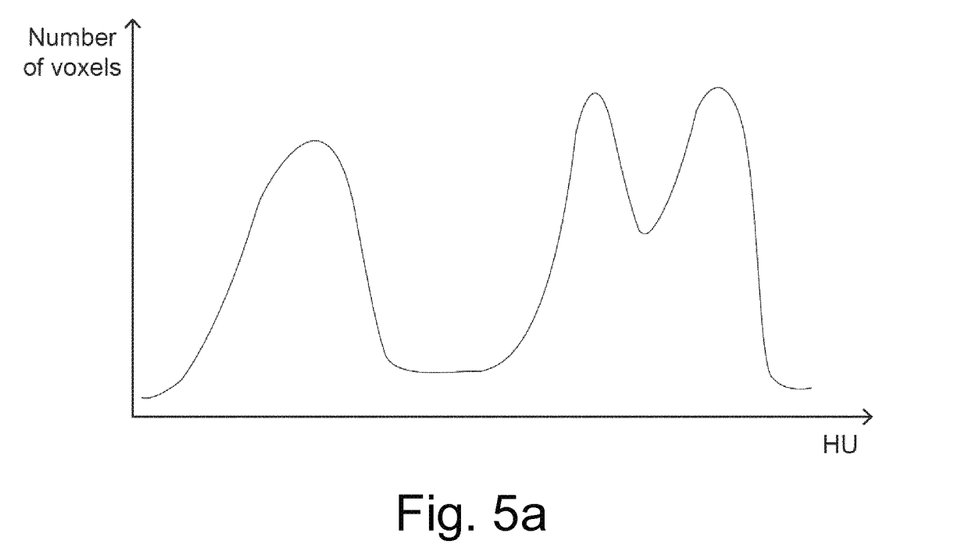
FIGS. 5a-5d are diagrams illustrating aspects of the method of FIG. 4.
Figure 5B:
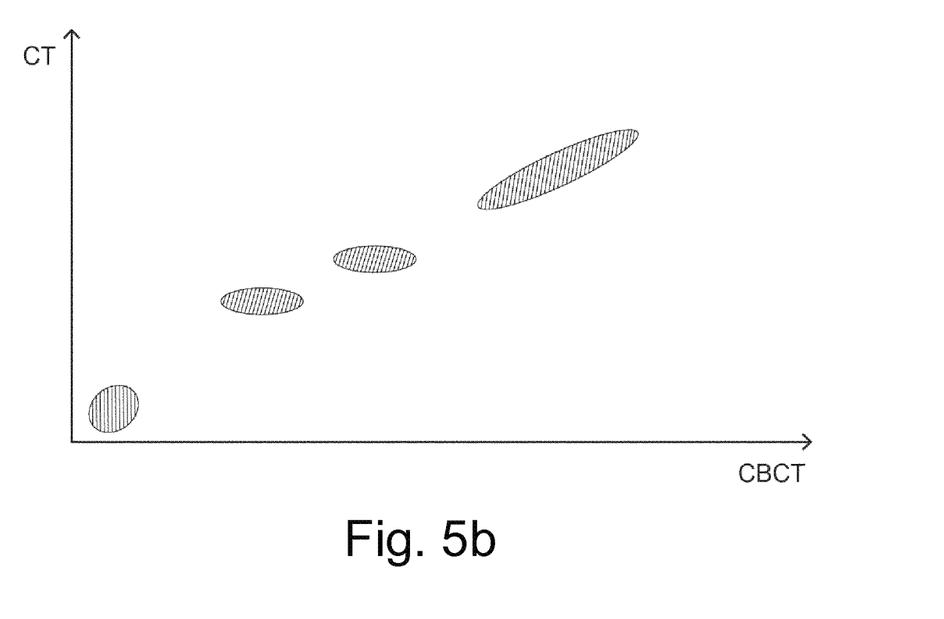

In step S43, a joint histogram is created based on the CT image, the CBCT image and the registration data. The registration data are used to match the value of each voxel of the CT image, with the corresponding value in the CBCT image to create value pairs. The number of occurrences of each value pair is stored in the joint histogram. A simplified example of such a joint histogram is shown in FIG. 5b. The joint histogram is used to find a set of tissue value pairs to be used in the transform between the CT image and the CBCT image or vice versa. Optionally, the joint histogram is smoothed by a suitable algorithm to remove noise.

Step S44 is an optional step, in which the number of tissue value pairs, and/or the actual values to be found in step S45 is decided. Further, for each of these tissue value pairs a restricted area in the joint histogram may be found. This may be done randomly, but is preferably based on a histogram showing the number of occurrences of the values of the CT image or of the CBCT image. The peak values in such a histogram correspond to different types of tissue in the image. The number of peaks, as well as the positions of the valleys between them, may be used to determine the number of tissue value pairs to be found or value restrictions that should be used. An example of such a histogram is shown in FIG. 5a. Also, or alternatively, a restriction may be set that tissue value pairs must be selected in such a way that they have a certain minimum distance between them. It would be possible at this stage also to select the values of the CT image that are to be matched with CBCT values to create value pairs. Typically, however, the CT values and the CBCT values are both identified in the joint histogram, as described in step S45.

In step S45 a number of tissue value pairs are identified, to be used for creating the transform representation, where appropriate in accordance with step S44. The tissue value pairs may be identified in any suitable way, but preferably based on the joint histogram. The tissue value pairs should be selected among the most frequently occurring value pairs in at least one of the images, which may be identified, for example, by finding peaks in the joint histogram. If step S44 is performed, the value pairs are identified in accordance with the information obtained in step S44, determining the number of tissue value pairs and their respective value range restrictions. It is feasible, but not necessary, to search for value pairs in restricted areas typically starting in one peak area and moving on to one or more other areas. These restricted areas can be determined in any suitable way, for example, based on their distances from previously found tissue value pairs and/or information obtained in step S44. The order in which the tissue value pairs are found is not crucial but may suitably be decided based on the peak size determined in step S44. The peaks can be handled in any suitable order, for example working from left to right in the diagram. One particularly feasible way would be to start searching for the tissue value pair corresponding to the largest peak in step S44, which would assure that the most common tissue type will be regarded first and thus cannot be excluded based on restrictions set by earlier found tissue value pairs. Then the next largest peak would be considered, and so on. It would also be possible, to set restrictions on following tissue value pairs that ensure that the transformation representation will be monotonically increasing.

Alternatively, in step S45, the value pairs may be selected as the maximum positions in the CT and CBCT histograms created from the joint histogram, or part of the joint histogram, by collapsing it in one or the other direction. Typically, only values below a certain density threshold, corresponding to bone, are considered, since bone should be considered separately.

Step S46 is an optional step in which a line or a match for bone tissues are identified. The values for bone tissues will be in the upper right part of the joint histogram. The match for bone tissues may be obtained in any suitable way, for example by linear regression or by using the RANSAC method. In general, for a line, the RANSAC method finds the line that maximizes the number of data points within a certain distance from the line. The line may be forced to connect to any previously found tissue value pair. Preferably, a number of points from this line are saved as tissue value pairs indicating bone tissues. This step could be performed at any suitable stage of the procedure.

This method is based on the assumption that while there will probably be some mismatches between the tissue types in the CT and CBCT images, most of the apparent overlaps will probably be correct, meaning that if a region in one image appears to be the same type of tissue as a corresponding region in the other image, this will probably be correct for a majority of the voxels in the region. Hence, the value pairs that occur most frequently in the joint histogram will correctly match the values in the CBCT image to the values in the CT image.

Figure 5C:
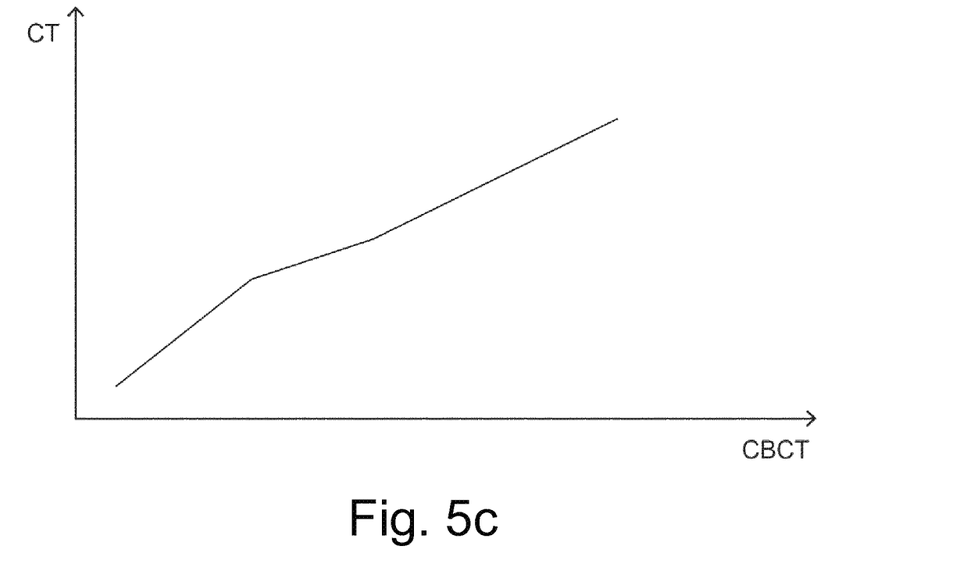

In step S47, interpolation is performed between the tissue value pairs generated in steps S45 and optionally S46, to create a representation of the transform between the CT image and the CBCT image, or vice versa. The representation may be in any suitable form, such as a function, a lookup table (LUT) or a diagram. Such a diagram is shown in FIG. 5c as a continuous line relating each value in the CT image to the corresponding value in the CBCT image. The representation may be adapted to a straight line, or to straight lines between the tissue value pairs generated in step S45, which may have different inclinations, or may have any other suitable shape. The representation can also incorporate information on tissue distribution width in the joint histogram, as shown in FIG. 5b, for example, to shape the transformation into plateaus around these areas, as exemplified in FIG. 5d. At the same time, a reversed transformation can be created for going from CT values to CBCT values, for use in the method of FIG. 2.

In step S48, the values in the CBCT image are transformed to the corresponding values from the CT image, or vice versa, using the representation obtained in step S47. As will be understood, the transformation may be performed at any suitable time after the representation has been made available.

Optionally, when identifying the tissue value pairs in step S45, prominent peaks in the joint histogram, that is, frequently occurring value pairs, can be identified. When a peak has been identified and selected as a tissue value pair, it may be suitable to discard any peaks close to the selected peak from further consideration. In any such case, the highest peak among the adjacent peaks should be selected. Correspondingly, value pairs that occur infrequently, and/or low regions in the histogram of CT values, should be actively avoided.

FIG. 5a shows, schematically, what a histogram such as the one referred to in Step S44 could look like. The horizontal axis represents the HU values and the vertical axis represents the number of voxels having each particular HU value. As illustrated by the curve, there will typically be some peaks corresponding to the most common types of tissue in the image and some low areas for which there are no or few voxels.

FIG. 5b shows a simplified joint histogram as obtained in step S43, with CBCT values along the horizontal axis and CT values along the vertical axis. The shaded areas correspond to value pairs indicative of different tissue types. The leftmost, lowermost shaded area corresponds to air, which has the lowest density values in both images. Typically (due to artefacts and noise), as shown, a wider range of CBCT values will be matched to a narrower range of CT values, resulting in somewhat oblong shaded areas in the diagram. The shaded area corresponding to the highest values represents bone tissue. These values will not normally be represented by a single tissue value pair, and will be treated specially, as discussed in connection with step S46.

FIG. 5c shows a resulting transformation, illustrated as a diagram in which lines have been inserted to join the shaded areas for FIG. 5b together to approximate matches between CBCT and CT values along the whole value range of the image.

Figure 5D:
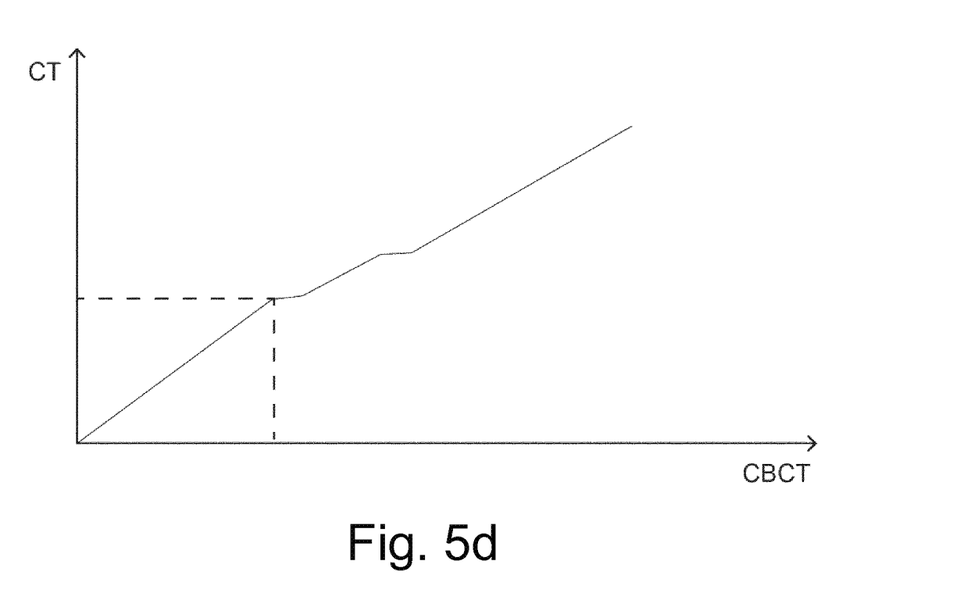

FIG. 5d shows an alternative diagram to the one shown in FIG. 5c. As can be seen, the curve has two plateaus, where each CT value is matched to a range of CBCT values. This reflects the common situation where a broad range of CBCT values corresponds to a narrower range of CT values. To obtain the CT value corresponding to any given CBCT value, simply find the point on the curve corresponding to the CBCT value along the horizontal axis and determine the matching CT value on the vertical axis, as illustrated by the dotted lines in FIG. 5d. A table or diagram creating a mapping in the opposite direction, that is enabling the CBCT value corresponding to a given CT value, may also be useful. Values may be represented in any suitable way in the table and/or diagram.

Figure 6:
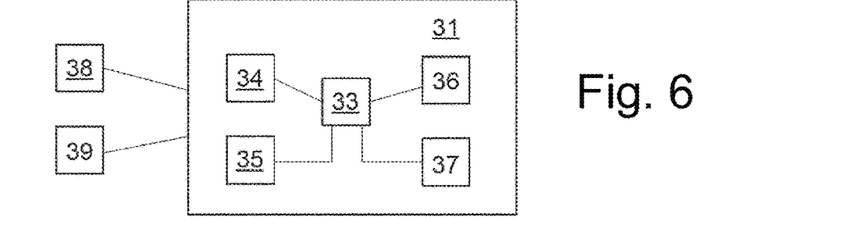
FIG. 6 is a schematic drawing of a computer system in which the method according to any embodiment of the invention may be implemented.

FIG. 6 is a schematic drawing of a computer system in which the method according to the invention may be performed. A computer 31 comprises a processor 33, a first and a second data memory 34, 35 and a first and a second program memory 36, 37. Preferably, one or more user input means 38, 39 are also present, in the form of a keyboard, a mouse, a joystick, voice recognition means or any other available user input means. The user input means may also be arranged to receive data from an external memory unit.

The first data memory 34 comprises at least one CT image and at least one corresponding CBCT image. The second data memory 35 holds data related obtained during the procedure, including the correction map and the mask. The first program memory 36 holds a computer program arranged to make the computer perform the method steps discussed in connection with FIGS. 2 and 3. The second program memory 37 holds a computer program arranged to make the computer perform the method steps discussed in connection with FIG. 4.

As will be understood, the data memories 34, 35 and the program memories 36, 37 are shown and discussed schematically. There may be several data memory units, each holding one or more different types of data, or one data memory holding all data in a suitably structured way, and the same holds for the program memories. For example, there may be separate memories or memory segments for different image modalities. One or more memories may also be stored on other computers.

The invention claimed is:

1. A method of correcting a first CT image of a region of a patient for artefacts, comprising the steps of:
   a) obtaining the first CT image and a corresponding second CT image as an original first and second CT image, respectively, and letting the original first CT image be the current first CT image;
   b) obtaining data representing a registration between the images;
   c) ensuring that the first and the second CT image use the same value range, thus forming a value matched image pair;
   d) obtaining a difference image D between the images of the value matched image pair;
   e) defining an image mask M defining which voxels to consider in the difference image;
   f) obtaining a final correction map Cf by an iterative method comprising the following steps:
      i. defining the correction map C based on the difference image and optionally the image mask M;
      ii. updating the final correction map Cf;
      iii. updating the first CT image using the correction map, and taking the updated image as the current first CT image;
      iv. updating the image mask M based on information from the correction map, the difference image and/or the current first and second CT image;
      v. updating the first or the second CT image of the value matched image pair based on the current first CT image;
      vi. calculating a difference image between the updated second CT image and the current first CT image; and
      vii. applying the final correction map to the original first CT image or to the current first CT image.

2. The method according to claim 1, wherein the step of ensuring that the first and the second CT image use the same value range comprises comparing the value ranges of the first and second CT image and if necessary convert the value range of the first or the second CT image to the value range of the other image.

3. The method according to claim 2, wherein the conversion is performed by means of a transform representation such as a function, a LUT or a diagram, said transform representation mapping a value in the first CT image to a value in the second CT image or vice versa.

4. The method according to claim 3, wherein said transform representation is obtained by a method comprising the following steps:
   providing the first and the second CT image and providing data representing a registration between the first and the second CT image;
   creating a joint histogram based on the registration data provided in step a);
   based on the joint histogram obtained in step b), identifying at least two tissue value pairs, each tissue value pair corresponding to a type of tissue or material found in the imaged object; and based at least some of the value pairs identified in step c), creating the representation of a transformation from the first CT image to the second CT image and/or vice versa.

5. The method according to claim 4, comprising the steps of creating a CT histogram of the occurrences of values in one of the images and, based on the occurrences, selecting the number of tissue value pairs and optionally restricting the area in the joint histogram for the step of identifying tissue value pairs.

6. The method according to claim 4, comprising the step of selecting the voxels to be used in identifying tissue value pairs, as voxels having a value below a threshold, preferably corresponding to the density of bone tissue and/or determining at least one tissue value pair for bone by identifying a line for values above the threshold, for example using the RANSAC method.

7. The method according to claim 6, further comprising forcing the line to pass through the point corresponding to the tissue value pair with the highest density below the bone density.

8. The method according to claim 1, wherein the image mask is defined so that it includes voxels for which the corresponding voxels in the difference image contain information about the artefacts to be corrected for, whilst excluding voxels containing information irrelevant or misleading to the correction.

9. The method according to claim 8, wherein the image mask includes voxels for which the absolute difference is below a threshold value and excludes voxels for which the difference is above the threshold value.

10. The method according to claim 1, wherein the steps of the loop i-vi are selected and iterated first to produce the image mask M then to produce the final correction map C.

11. The method according to claim 10, wherein the steps of the loop of step f) i-vi are selected and iterated in the following manner:
   i. updating the image mask by an iterative method including the following steps:
      i. defining the correction map C based on the difference image and optionally the image mask M;
      ii. updating the first CT image using the correction map, and taking the updated image as the current first CT image;
      iii. updating the image mask M based on information from the correction map, the difference image and/or the current first and second CT image;
      iv. updating the first or the second CT image of the value matched image pair based on the current first CT image;
      v. calculating a difference image between the updated second CT image and the current first CT image;
   ii. defining the correction map C based on the difference image and optionally the image mask M, said correction map indicating which areas of the CBCT image should be corrected and by how much;
      i. defining the correction map C based on the difference image and optionally the image mask M;
      ii. updating the final correction map Cf;
      iii. updating the first CT image using the correction map, and taking the updated image as the current first CT image;
      iv. updating the first or the second CT image of the value matched image pair based on the current first CT image;
      v. calculating a difference image between the updated second CT image and the current first CT image; and
   h) applying the final correction map to the original first CT image or to the current first CT image.

12. A computer program product comprising non-transitory computer-readable code means which, when run in a computer will cause the computer to perform the method according to claim 1.

13. A computer system comprising a processor for executing computer programs and program memory holding a computer program product according to claim 12.

14. A treatment planning system for calculating radiation therapy treatment plans, comprising a computer system according to claim 13.

* * * * *